United States Patent [19]

Fields, Jr.

[11] Patent Number: 5,043,475

[45] Date of Patent: Aug. 27, 1991

[54] PEROXIDE PROCESS FOR PRODUCING N-PHOSPHONOMETHYLGLYCINE

[75] Inventor: Donald L. Fields, Jr., Manchester, Mo.

[73] Assignee: Monsanto Company, St. Louis, Mo.

[21] Appl. No.: 542,995

[22] Filed: Jun. 25, 1990

[51] Int. Cl.$^5$ .............................................. C07F 9/38
[52] U.S. Cl. ..................................................... 562/17
[58] Field of Search ........................................ 562/17

[56] References Cited

U.S. PATENT DOCUMENTS

| | | | |
|---|---|---|---|
| 3,950,402 | 4/1976 | Franz | 260/502.5 |
| 3,954,848 | 5/1976 | Franz | 260/502.5 |
| 4,062,669 | 12/1977 | Franz | 562/17 |
| 4,579,689 | 4/1986 | Hershman et al. | 562/17 |
| 4,582,650 | 4/1986 | Felthowe | 562/17 |
| 4,853,159 | 8/1989 | Riley et al. | 562/17 |
| 4,898,972 | 2/1990 | Fields et al. | 562/17 |
| 4,952,723 | 8/1990 | Fields et al. | 562/17 |

FOREIGN PATENT DOCUMENTS 0187347  7/1981  Hungary .

*Primary Examiner*—J. E. Evans
*Attorney, Agent, or Firm*—Frank D. Shearin

[57] ABSTRACT

A process is provided for producing N-phosphonomethylglycine by the oxidation of N-phosphonomethyliminodiacetic acid with a peroxide to form an intermediate N-phosphonomethyliminodiacetic acid-N-oxide. Thereafter, the N-phosphonomethyliminodiacetic acid-N-oxide is converted to N-phosphonomethylglycine by adding a catalytic amount of a metal selected from the group consisting of iron, zinc, aluminum, vanadium and copper, or a compound selected from the group consisting of water-soluble vanadium compounds, ferrous salts and cuprous salts.

5 Claims, No Drawings

PEROXIDE PROCESS FOR PRODUCING N-PHOSPHONOMETHYLGLYCINE

BACKGROUND OF THE INVENTION

This invention relates to a process for the preparation of N-phosphonomethylglycine, and more particularly to the preparation of N-phosphonomethylglycine by the conversion of N-phosphonomethyliminodiacetic acid to N-phosphonomethylglycine using peroxides.

N-Phosphonomethylglycine, known also by its common name glyphosate, is a highly effective, commercially important, phytotoxicant useful in controlling a large variety of weeds. It is applied to the foliage of a very broad spectrum of annual and perenial grasses and broadleaf plants. Industrial uses include control of weeds along roadsides, waterways, transmission lines, in storage areas, and in other nonagricultural areas. Usually, N-phosphonomethylglycine is formulated into herbicidal compositions in the form of its various salts in solution, preferably water.

U.S. Pat. No. 3,950,402 to Franz discloses a process for the production of N-phosphonomethylglycine by forming an admixture of N-phosphonomethyliminodiacetic acid, water, and a metallic catalyst selected from the noble metals, heating the admixture to an elevated temperature (greater than 70° C. to avoid low yields) and contacting the admixture with a free oxygent-containing gas.

U.S. Pat. No. 3,954,848 to Franz discloses a process for the production of N-phosphonomethylglycine by reacting N-phosphonomethyliminodiacetic acid with an oxidizing agent, such as hydrogen peroxide, in an aqueous acidic medium in the presence of a strong acid at a temperature of from about 70° C. to about 100° C. It is disclosed that one should employ at least 2 moles of the hydrogen peroxide for each mole of the N-phosphonomethyliminodiacetic acid, and preferably more.

Hungarian Patent Application No. 187,347 discloses a process for the preparation of N-phosphonomethylglycine by the oxidation of N-phosphonomethyliminodiacetic acid with peroxides using a catalytic amount of a metal compound selected from compounds of silver, iron, tin, lead, manganese or molybdenum. Molybdates are preferred. At temperatures lower than 80° C., usually a contaminated end product is obtained. Typically, the reaction is carried out at a temperature of above 80° C. and preferably above 100° C. at pressures exceeding atmospheric, wherein the intermediate N-oxide is decomposed as rapidly as it forms. It is further disclosed that two mole equivalents of peroxide should be used for each mole of N-phosphonomethyliminodiacetic acid to obtain acceptable yields of N-phosphonomethylglycine.

Although satisfactory results are obtained by the above processes to make N-phosphonomethylglycine, all of them suffer from one or more disadvantages, such as the use of excessive amounts of peroxide, the use of strong mineral acids and/or reaction at elevated temperatures and pressures. Now, there is provided a process which produces N-phosphonomethylglycine in high yields at modest temperatures and at atmospheric pressure using substantially stoichiometric amounts of peroxide to oxidize the N-phosphonomethyliminodiacetic acid to the desire N-phosphonomethylglycine without using strong mineral acids, such as hydrochloric acid or sulfuric acid.

SUMMARY OF THE INVENTION

These and other advantages are achieved in a process for producing N-phosphonomethylglycine by the oxidation of N-phosphonomethyliminodiacetic acid with peroxide to form an intermediate N-phosphonomethyliminodiacetic acid-N-oxide, the improvement which comprises adding a catalytic amount of a metal selected from the group consisting of iron, zinc, aluminum, vanadium and copper, or a compound selected from the group consisting of water-soluble vanadium salts, ferrous salts, and cuprous salts.

DETAILED DESCRIPTION OF THE INVENTION

The intermediate, N-phosphonomethyliminodiacetic acid-N-oxide, is known to those skilled in the art, and can be prepared by a number of methods. For example, the intermediate can be prepared by the teachings in U.S. Pat. No. 3,950,402 or U.S. Pat. No. 3,954,848, both to Franz. In Hungarian Patent Application 187,347, the intermediate is formed from N-phosphonomethyliminodiacetic acid using peroxides in the presence of compounds of silver, iron, tin, lead, manganese or molybdenum. In U.S. Pat. No. 4,062,669 to Franz, an N-organo-N-phosphonomethylglycine is oxidized with peroxide under acidic or basic conditions. Other methods may be known to those skilled in the art.

Any number of peroxides known to those skilled int he art can be used to prepare the N-phosphonomethyliminodiacetic acid-N-oxide. Suitable peroxides include hydrogen peroxide, performic acid, peracetic acid, perbenzoic acid, peroxytrifluoroacetic acid, benzoyl peroxide, benzenepersulfonic acid, and the like. Hydrogen peroxide is preferred, and it is advantageous to use hydrogen peroxide in the form of a concentrated solution, say between about 30% and 60%.

In the process of the present invention, it is preferred to prepare the N-phosphonomethyliminodiacetic acid-N-oxide by contacting N-phosphonomethyliminodiacetic acid with a peroxide in the presence of a catalytic amount of a water-soluble molybdenum compound or a water-soluble tungsten compound. A water-soluble tungsten compound is especially preferred.

The temperature of the process to prepare the N-phosphonomethyliminodiacetic acid-N-oxide can vary from as low as about 20° C. to about 70° C. Although temperatures below about 20° C. can be used, such temperatures would require the use of cooling, and no advantages are obtained. At temperatures above about 70° C., degradation of the N-phosphonomethyliminodiacetic acid-N-oxide is observed, which affects the final yield of the desire N-phosphonomethylglycine. Temperatures between about 20° C. and about 65° C. are preferred.

The salts of tungsten useful as catalysts to oxidize the N-phosphonomethyliminodiacetic acid to the N-phosphonomethyliminodiacetic acid-N-oxide are known to those skilled in the art. It is only necessary that the tungsten salts are soluble in the reaction medium. Suitable tungsten compounds include tungstic acid, 1,2-tungstophosphate, and barium tungstate. The alkali metal tungstates, such as sodium tungstate, potassium tungstate, and the like, provide satisfactory results, and the alkali metal tungstates are preferred.

The salts of molybdenum useful as catalysts to oxidize the N-phosphonomethyliminodiacetic acid to the N-phosphonomethyliminodiacetic acid-N-oxide are also known to those skilled in the art. It is only necessary that the molybdenum salts are soluble in the reaction medium. Suitable molybdenum compounds include molybdenum halides, such as molybdenyl trichloride and the like, alkali metal molybdates, such as sodium molybdate and the like, or more complex salts, such as the ammonium or alkali metal dimolybdates. Sodium and ammonium molybdates are preferred.

The amount of catalyst to convert the N-phosphonomethyliminodiacetic acid to the intermediate N-phosphonomethyliminodiacetic acid-N-oxide can vary within wide limits. Concentrations between about 0.01 and about 5 wt. % catalyst, based on the weight of the N-phosphonomethyliminodiacetic acid, provide satisfactory results. At concentrations of less than about 0.01 wt. % catalyst, the reaction is slow, and at concentrations greater than about 5 wt. %, no particular advantage is seen, although such higher concentrations are not harmful. It is preferred to use between about 0.01 wt. % and about 1 wt. % based on the weight of the N-phosphonomethyliminodiacetic acid.

In the process of the present invention, the amount of peroxide should be the stoichiometric amount required to convert the N-phosphonomethyliminodiacetic acid to the intermediate N-phosphonomethyliminodiacetic acid-N-oxide. As will occur to those skilled in the art, when less than the stoichiometric amount of peroxide is used, the yield of the desired N-phosphonomethylglycine is lower. A slight excess of peroxide can be used to insure a quantitative conversion of the N-phosphonomethyliminodiacetic acid to the intermediate, but there is no advantage to using large excesses of peroxide, and excesses of peroxide may be deleterious if water-soluble compounds, such as ferrous salts or cuprous salts, are used to convert the intermediate to N-phosphonomethylglycine.

Regardless of the method used to prepare the N-phosphonomethyliminodiacetic acid-N-oxide from the N-phosphonomethyliminodiacetic acid, the intermediate is contacted with a catalytic amount of a substance selected from the group consisting of iron metal, zinc metal, aluminum metal, vanadium metal or copper metal. Alternatively, a compound selected from the group consist of the water-soluble salts of a vanadium compound, ferrous salts, and cuprous salts can convert the intermediate N-phosphonomethyliminodiacetic acid-N-oxide to the desired N-phosphonomethylglycine. Suitable vanadium compounds that are soluble in the reaction mixture include vanadium pentoxide, vanadium sulfate, vanadium chloride and the like. Suitable water-soluble ferrous compounds that can be used in the process of the present invention include ferrous sulfate, ferrous halides, such as ferrous chloride, ferrous bromide and the like. Suitable water-soluble cuprous salts that can be used in the process of the present invention include cuprous chloride, cuprous bromide, cuprous sulfate and the like. Of the water-soluble compounds, vanadium compounds are preferred, and vanadyl sulfate is especially preferred.

The amount of catalyst to convert the N-phosphonomethyliminodiacetic acid-N-oxide to N-phosphonomethylglycine depends upon the catalyst used and the amount of peroxide in excess of that required to produce the intermediate from the N-phosphonomethyliminodiacetic acid. When metals such as iron, zinc, aluminum, vanadium and copper are used, the rate of reaction to convert the intermediate N-phosphonomethyliminodiacetic acid-N-oxide to N-phosphonomethylglycine depends upon the surface area of the metal present, and it is preferred to use from about 0.1 wt. % to about 10 wt. % of the metal, based on the weight of the N-phosphonomethyliminodiacetic acid-N-oxide present. In addition, it is preferred to use the metal in any form that provides a high surface area, for example, a wool, a powder or finely divided granules. However, when a water-soluble compound is used as a catalyst, the excess peroxide will react with the water-soluble compound, and in addition to the amount of compound required to react with the excess peroxide, there should also be a sufficient amount of the water-soluble compound to catalyze the reaction of the N-phosphonomethyliminodiacetic acid-N-oxide to N-phosphonomethylglycine. The amount of water-soluble compound remaining after reaction with the peroxide to act as a catalyst should be at least 0.005 wt. %, based on the amount of the N-phosphonomethyliminodiacetic acid-N-oxide. Excess water-soluble compound as high as 5%, or even higher, can be used, but there does not seem to be an advantage to using such higher concentrations for the conversion of the intermediate to N-phosphonomethylglycine, although such higher concentrations are not harmful. It is preferred to use between about 0.01 wt. % and about 2 wt. % of the water-soluble compound, based on the weight of the N-phosphonomethyliminodiacetic acid-N-oxide, after reaction with any excess peroxides.

The temperature required to convert the intermediate N-phosphonomethyliminodiacetic acid-N-oxide to the desired N-phosphonomethylglycine can vary within wide limits. It is preferred to add the catalyst at or near room temperature (about 20° C.) because vigorous gas evolution frequently occurs, and the conversion of N-phosphonomethyliminodiacetic acid-N-oxide to N-phosphonomethylglycine is exothermic. It is preferred to keep the reaction temperature below about 80° C. by cooling the reaction vessel or using a low catalyst charge. Temperatures above about 80° C. will provide N-phosphonomethylglycine, but some yield loss may occur.

The concentration of the N-phosphonomethyliminodiacetic acid as the starting material can vary within wide limits in the process of the present invention. For example, an aqueous suspension containing up to 50 wt. % N-phosphonomethyliminodiacetic acid can used. Higher concentrations of the N-phosphonomethyliminodiacetic acid can be used, but it can present processing difficulties because of the thickness of the slurry. On the other hand, an aqueous solution of the N-phosphonomethyliminodiacetic acid containing about 5 wt. % of the N-phosphonomethyliminodiacetic acid can also be used. Lower concentrations can also be used, but it requires processing large volumes of liquid in the process of the present invention. It is preferred to use an aqueous slurry containing from about 20 wt. % to about 40 wt. % of the N-phosphonomethyliminodiacetic acid.

The N-phosphonomethyliminodiacetic acid starting material can be prepared by methods known to those skilled in the art. For example, this material can be produced by the reaction of formaldehyde, iminodiacetic acid and orthophosphorous acid in the presence of sulfuric acid. Although the N-phosphonomethyliminodiacetic acid mixture resulting from this reaction can be employed directly in the process of this invention, it is preferred to isolate the N-phosphonomethyliminodiacetic acid and then employ it herein.

This invention is further illustrated by, but not limited to, the following examples. Conversion is calculated by dividing the moles of other compounds produced by the moles of starting N-phosphonomethyliminodiacetic acid and multiplying by 100. Selectivity is calculated by dividing the moles of N-phosphonomethylglycine produced by the moles of N-phosphonomethyliminodiacetic acid converted and multiplying by 100.

EXAMPLE 1

This Example illustrates the process of the present invention using a water-soluble vanadium salt to convert the intermediate N-phosphonomethyliminodiacetic acid-N-oxide to N-phosphonomethylglycine.

(A) To a 100 ml round bottomed flask was added water (25 ml), N-phosphonomethyliminodiacetic acid (20 g), 47% hydrogen peroxide (7.1 g) and sodium tungstate (0.05 g). The mixture was heated to 65° C. and maintained at this temperature until a solution was obtained (about 58 minutes), indicating the N-oxide was formed. The solution was then allowed to cool to about 55° C. and stirred for an additional 30 minutes.

(B) After cooling to room temperature, vanadyl sulfate (0.05 g, 29% water content) was added to the solution. After stirring for about 5 minutes, the color of the solution changed from blue to light green. Gas evolution began with a slow exotherm. When the temperature reached about 40° C., the exotherm greatly accelerated to 65° C. and cooling water was applied to maintain the solution at this temperature. The reaction mixture was allowed to cool to room temperature, the solids were filtered, and the filtrate and solids were analyzed by HPLC. The conversion of N-phosphonomethyliminodiacetic acid was 96.7%, and the selectivity to N-phosphonomethylglycine was 91.4%.

EXAMPLE 2

This Example illustrates the process of the present invention using a water-soluble ferrous salt to convert the intermediate N-phosphonomethyliminodiacetic acid-N-oxide to N-phosphonomethylglycine.

The procedure of Example 1 Step (A) was repeated. Then after the solution was allowed to cool to room temperature, ferrous sulfate (0.02 g) was added to the solution. Gas evolution was observed, and the temperature of the solution rose to 65° C. Cooling water was applied to keep the temperature below 70° C. The reaction mixture was allowed to cool to room temperature, the solids were filtered, and the filtrate and solids were analyzed by HPLC. The conversion of N-phosphonomethyliminodiacetic acid was 99.5%, and the selectivity to N-phosphonomethylglycine was 93.7%.

EXAMPLE 3

This Example illustrates the process of the present invention using zinc metal to convert N-phosphonomethyliminodiacetic acid-N-oxide to N-phosphonomethylglycine.

(A) To a 100 ml round bottomed glass flask was added water (37 ml), N-phosphonomethyliminodiacetic acid (14.0 g), 30% hydrogen peroxide (7.2 g) and ammonium dimolybdate tetrahyrate (0.32 g). The mixture was heated to 65° C. and maintained at this temperature until a solution was obtained (about 30 minutes), indicating the N-oxide was formed. The solution was then allowed to cool to 45° C. and stirred for 50 minutes.

(B) After cooling to room temperature, zinc metal powder (0.4 g) was added to the solution. Vigorous gas evolution was observed, and the temperature of the solution rose to 55° C. in about a 10-minute period. The reaction mixture was allowed to cool to room temperature, the solids were filtered, and the filtrate and solids were analyzed by HPLC. The conversion of N-phosphonomethyliminodiacetic acid was 91.0%, and the selectivity to N-phosphonomethylglycine was 93.8%.

EXAMPLE 4

This Example illustrates the use of copper metal, aluminum metal, and a water-soluble cuprous salt to convert the intermediate N-phosphonomethyliminodiacetic acid-N-oxide to N-phosphonomethylglycine.

The procedure of Example 3 Step (A) was repeated. After cooling to room temperature, small aliquots of the solution containing the N-phosphonomethyliminodiacetic acid-N-oxide were taken and placed in 25 ml beakers. To one aliquot was added a copper penny. To another aliquot was added aluminum foil. To a third aliquot was added a small amount of cuprous chloride. and to a fourth aliquot was added vanadium metal. In all cases, gas evolution was observed, indicating that the intermediate N-phosphonomethyliminodiacetic acid-N-oxide was converted to N-phosphonomethylglycine.

Although the invention has been described in terms of specified embodiments which are set forth in considerable detail, it should be understood that this is by way of illustration only, and that alternative embodiments and operating techniques will become apparent to those skilled in the art in view of the disclosure. Accordingly, modifications can be made without departing from the spirit of the described invention.

What is claimed is:

1. In a process for producing N-phosphonomethylglycine by the oxidation of N-phosphonomethyliminodiacetic acid with a peroxide to form an intermediate N-phosphonomethyliminodiacetic acid-N-oxide, the improvement which comprises adding a catalytic amount of a metal selected from the group consisting of iron, zinc, aluminum, vanadium and copper to convert the intermediate to N-phosphonomethylglycine.

2. In a process of claim 1 wherein the catalytic amount of the metal is between about 0.1 wt. % and about 10 wt. %, based on the weight of the N-phosphonomethyliminodiacetic acid-N-oxide.

3. In a process of claim 2 wherein the catalyst is iron metal.

4. In a process of claim 1 wherein the amount of catalyst to convert the intermediate N-phosphonomethyliminodiacetic acid-N-oxide is between about 0.005 wt. % and about 5 wt. %, based on the weight of the N-phosphonomethyliminodiacetic acid-N-oxide present.

5. In a process of claim 1 wherein the amount of catalyst is between about 0.01 wt. % and about 2.0 wt. %.

* * * * *